US009316620B2

(12) United States Patent
Xiang et al.

(10) Patent No.: US 9,316,620 B2
(45) Date of Patent: Apr. 19, 2016

(54) STRUCTURAL DAMAGE DETECTION SYSTEM, DEVICE AND METHOD

(75) Inventors: Zhihai Xiang, Beijing (CN); Qiuhai Lu, Beijing (CN); Xiaowei Dai, Beijing (CN); Yao Zhang, Beijing (CN)

(73) Assignee: Tsinghua University, Beijing (CN)

( * ) Notice: Subject to any disclaimer, the term of this patent is extended or adjusted under 35 U.S.C. 154(b) by 1051 days.

(21) Appl. No.: 13/320,260

(22) PCT Filed: Apr. 9, 2010

(86) PCT No.: PCT/CN2010/000470
§ 371 (c)(1),
(2), (4) Date: Nov. 12, 2011

(87) PCT Pub. No.: WO2010/130144
PCT Pub. Date: Nov. 18, 2010

(65) Prior Publication Data
US 2012/0059600 A1   Mar. 8, 2012

(30) Foreign Application Priority Data
May 13, 2009   (CN) .......................... 2009 1 0083772

(51) Int. Cl.
*G01B 5/30*     (2006.01)
*G01N 29/04*    (2006.01)
(Continued)

(52) U.S. Cl.
CPC ............ *G01N 29/045* (2013.01); *G01N 29/265* (2013.01); *G01N 29/348* (2013.01); *G01N 29/4409* (2013.01); *G01N 2291/0289* (2013.01)

(58) Field of Classification Search
CPC .......... G01N 29/045; G01N 2291/044; G01N 29/11; G01N 29/265; G01N 29/4409; G01N 2291/0289

USPC ........................................... 702/39
See application file for complete search history.

(56) References Cited

U.S. PATENT DOCUMENTS 7,240,554 B2   7/2007  Berke
2005/0072234 A1*  4/2005  Zhu et al. .................. 73/579
(Continued)

FOREIGN PATENT DOCUMENTS

CN   1804612     7/2006
CN   101561379   10/2009
(Continued)

OTHER PUBLICATIONS

English translation of JP 2006-349628, Dec. 2006.*
(Continued)

*Primary Examiner* — Michael Nghiem
(74) *Attorney, Agent, or Firm* — Arthur Tan-Chi Yuan (57) ABSTRACT

The present invention relates to a structural damage detection method for detecting damage of a structure. The method comprises scanning the surface of the structure with a tapper tapping with a tapping force at a predetermined frequency band while scanning; measuring the response signals transmitted from the surface of the structure; transforming the measured signals to acquire the signal spectrum at each position of the structure surface; intercepting from the signal spectrum a spectrum envelope; calculating a damage indicator at each position of the structure surface; and determining a position where the damage indicator changes abruptly as a position of structural damage. The present invention further relates to a structural damage detection system utilizing the structural damage detection method and a structural damage detection device for use therein.

11 Claims, 5 Drawing Sheets

(51) Int. Cl.
*G01N 29/265* (2006.01)
*G01N 29/34* (2006.01)
*G01N 29/44* (2006.01)

(56) References Cited

U.S. PATENT DOCUMENTS

2011/0040496 A1* 2/2011 Banerjee et al. ............... 702/34
2011/0314915 A1* 12/2011 Adams ............... G01M 5/0033
   73/582
2015/0323413 A1* 11/2015 Zhang ............... G01M 5/0008
   702/35

FOREIGN PATENT DOCUMENTS

CN 101561379 A * 10/2009
JP 2006-349628 A 12/2006

OTHER PUBLICATIONS

English Abstract of CN 101561379, Oct. 2009.*
International Search Report, Jul. 22, 2010.
Written Opinion of the International Searching Authority, Jul. 22, 2010.

* cited by examiner

STRUCTURAL DAMAGE DETECTION SYSTEM, DEVICE AND METHOD

TECHNICAL FIELD

The present invention relates to a structure damage detection system, device and method, in particular, to a structure damage detection system, device and method that detect damage of an engineering structure nondestructively.

BACKGROUND

Due to problems of the techniques or the use of load, some local damage, such as cracks, pits, debonding, is often found in an engineering structure during the manufacture and the usage, and such damage will affect the normal use of the structure when accumulated to a certain degree. In order that the structure can be normally operated, it is necessary to carry out a damage detection before it is put into service or after it has been used for a time period. For instance, a bridge has to undergo bridge testing before open to traffic so as to ensure that the design requirements are satisfied; during the service, periodical routine detections or non-periodical special detections are performed to detect damage of the structure timely. As another example, for aerial structures such as wing skin, they cannot be put into service until the degree of internal damage is lower than a prescribed threshold, and after a period of service, damage detection of these structures is required again to ensure the security of future flights.

Usually, detection of the engineering structures should not bring them further damage, so such detection methods are also called techniques of nondestructive detection of structures. The current techniques of nondestructive detection of structures are generally divided into two categories, namely local detection and overall detection:

Local detection technique performs damage detection through the observation of the naked human eyes or by means of X-ray, infrared-ray, ultrasound waves, radar, magnetic eddy current, etc. Although such technique boasts of high accuracy in damage detection for local regions, if the general damaged region is not known before hand, it will be quite time-consuming to detect successively each region of the engineering structure with this technique. Besides, some engineering structures have blind corners that cannot be detected with the local detection technique.

Overall detection technique measures responses of the engineering structures, such as static displacement, velocity and acceleration, under an external excitation by arranging sensors in the engineering structure, based on which the damage of the engineering structure is deduced. If the sensor is pre-installed in the engineering structure in advance, a real time monitoring of the damage can be achieved, but in this case, only the structural responses excited by the environmental excitation during operation of the engineering structure can be used for damage detection. Compared with the local detection technique, the overall detection technique has higher detection efficiency. However, it also has following disadvantages. Firstly, if the external excitation is not applied appropriately, the response of the engineering structure may not reflect the damage sufficiently, thereby affecting the accuracy of the detection. For example, if the static load is not large enough to fully open the cracks in the engineering structure, the static displacement will not be sensitive to the damage. Furthermore, as damage is a local feature of the engineering structure and its affects on the structural dynamic properties are often only reflected in high order frequency bands, if the external excitation cannot excite a response from the high order frequency bands of the engineering structure, the accuracy of damage deduction will be poor, and in turn, the accuracy of the result obtained by the overall detection will also be poor. Moreover, the overall detection technique is further confronted with the problems of reasonable arrangement of sensors, durability of sensors, interference of environmental noise, collection and transmission of signals, etc.

A tapping method based on the tapping mechanical model established by Cawley can detect damage in composite laminates. In the tapping mechanical model, it is considered that when a hammer taps a portion of structural damage, the time history signal of the tapping force on this portion has smaller peaks and larger widths than the signal of the tapping force generated by a tap on an intact portion due to the reduction of local stiffness. Based on that, a property parameter R can be obtained by calculating the area surrounded by the spectrum curve of the tapping force and the coordinate axis of the frequency, and damage can be identified by comparing the values of R of the intact portion and the damaged portion. Besides, the damage can also be identified by directly comparing the widths of the time history signal of the tapping force before and after the damage. The tapping method is also a local detection technique, which does not require fixing sensors on the structure. As the changes in the local stiffness of the structure can be collected, the method is very sensitive to damage. Nevertheless, this method utilizes the spectrum information of the tapping force over the entire frequency band, which reduces the accuracy of the damage identification to some degree, due to the following considerations: (1) damage is often reflected in the high order frequency band of the tapping force, and the use of information of the entire frequency band will mask information of a frequency band sensitive to the damage; (2) information of the entire frequency band comprises components of environmental noise. Moreover, the frequency range covered by the spectrum of the tapping force is determined by the structural stiffness and the stiffness of the hammer. In order to acquire a spectrum of high order frequency band, a hammer having high stiffness can be used, but this cannot accurately control the range of the spectrum. Even if high order spectrums can be excited, the high frequency components usually account for a small percentage in the entire frequency band, which will also affect the accuracy of damage detection. Finally, the method requires knowing the property parameters of the intact structure in advance, which brings inconveniency to the use. The current tapping damage detection devices can only reliably detect damage having a diameter larger than about 10 mm in a 2 mm thick structure.

In the field of damage detection of bridges, Yang et al. put forth a method of extracting the fundamental frequency of a bridge by using the acceleration signal of driving vehicles with the vehicles as excitations. The method has the merits that no sensors are required to be installed in the bridge and that the measurement procedure will not affect the normal operation of the bridge. However, in this method, no tapping means are installed in the vehicles, so it is difficult to excite higher frequency responses from the bridge and the obtained acceleration signal is insensitive to the local damage, whereas it is difficult to detect the damage of the structure merely based on the fundamental frequency of the bridge.

Therefore, it is desired to provide a structural damage detection method and a structural damage detection device capable of detecting damage of an engineering structure conveniently, rapidly and accurately without knowing the intact property information of the engineering structure in advance.

SUMMARY

In light of the above problems, the present invention is put forth so as to provide a structural damage detection method and a structural damage detection device that can overcome the above problems or at least partly solve the problems.

According to an aspect of the present invention, a structural damage detection method for detecting damage of a structure is provided. In this method, a tapper is used to scan along the surface of the structure, during scan, the tapper taps with a tapping force at a predetermined frequency band. Then a sensor is used to measure response signals transmitted from the structure surface to the tapper at each position of the structure surface. The signals measured by the sensor can be at least one of displacement, velocity and acceleration. The signals measured by the sensor are converted to acquire a frequency spectrum or a scale spectrum of the signal at each position of the structure surface. A spectrum envelope corresponding to the predetermined frequency band of the tapping force is intercepted from the spectrum of the signal; and the damage indicator at each position of the structure surface which reflects the degree of similarity between the spectrum envelope at this position and the spectrum envelope at other positions is calculated. In this method, a position where the damage indicator changes abruptly is determined as a position of structural damage.

According to a further aspect of the present invention, a structural damage detection device is provided. This device comprises a tapper configured to tap on the surface of the structure under detection with a tapping force at a predetermined frequency band; and a sensor configured to measure the response signals transmitted from the surface of the structure under detection to the tapper. The response signals measured by the sensor can be at least one of displacement, velocity and acceleration. The tapper and the sensor are integrated together, so that the sensor measures the response signals transmitted from the surface of the structure under detection to the tapper while the tapper is tapping on the surface of the structure under detection.

According to a further aspect of the present invention, a structural damage detection system is provided. This system comprises a structural damage detection device as described above, and a signal processor being configured to process the signals measured by the sensor in the structural damage detection device so as to determine the position of damage in the structure under detection. The signal processor comprises a spectrum acquisition unit being configured to convert the signals measured by the sensor so as to acquire the frequency spectrum or scale spectrum of the signal at each position of the structure surface, a spectrum envelope interception unit being configured to intercept from the signal spectrum a spectrum envelope corresponding to the predetermined frequency band of the tapping force, a damage indicator calculation unit being configured to calculate the damage indicator at each position of the structure surface, the damage indicator reflecting the degree of similarity between the spectrum envelope at this position and the spectrum envelope at other positions; and a damage position determining unit being configured to determine a position of damage in the structure based on the damage indicator at each position of the structure surface.

The magnitude and frequency band of a tapping force can be set in the method, device and system proposed in the present invention, which both helps to excite damage information and avoids interference of the environmental noise. In addition, only the responses transmitted from the surface of the structure under detection to the tapper and the response signals of a frequency band corresponding to the frequency band of the tapping force are processed, which can improve the accuracy of detection.

Besides, the method, device and system for structure damage detection according to the present invention do not require knowing any property information about the intact structure, so it is easier for implementation. This method, device and system are adapted to be applicable in any fields where various kinds of damage of structural materials are possible to be occurred, such as in field of aeronautics and astronautics, civil engineering, mechanics and so on.

BRIEF DESCRIPTION OF THE DRAWINGS

Other advantages and benefits of the present invention will be clear and obvious to those skilled in the art from the following detailed description. The drawings are only used for the purpose of showing the embodiments and should not be construed as limiting the invention. The same reference signs represent the same components throughout the drawings, specifically.

DETAILED DESCRIPTION

Further descriptions of the present invention are given as follows in combination with the figures and the specific embodiments.

Figure 1:
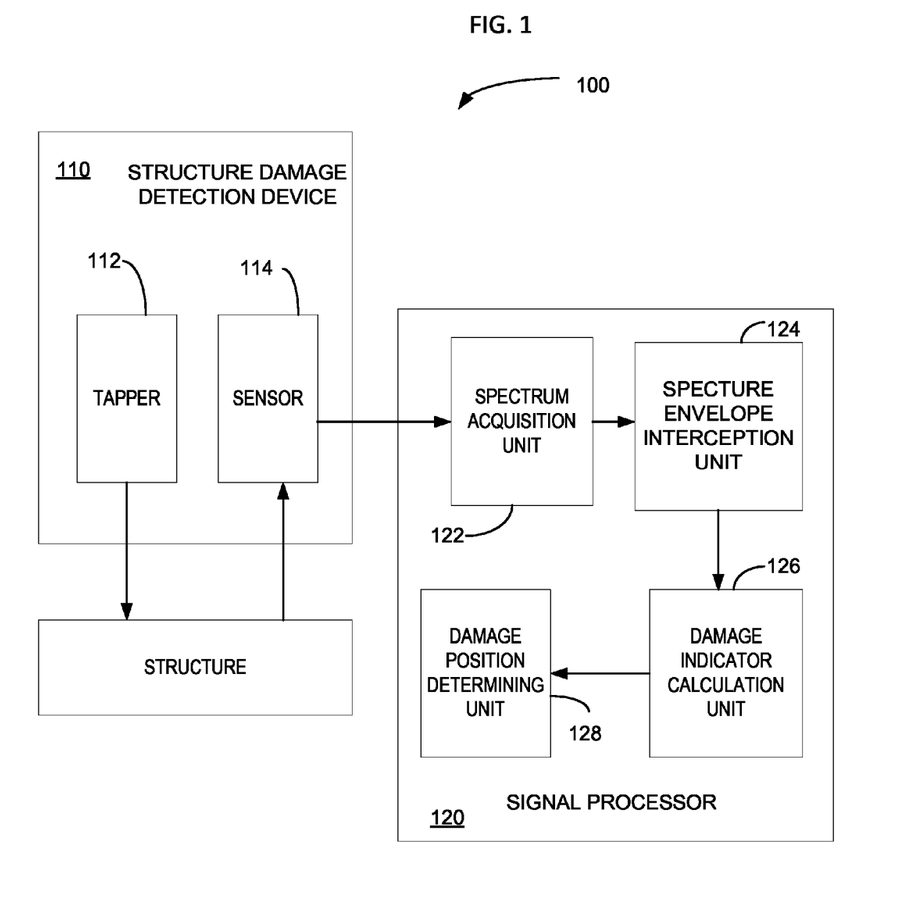
FIG. 1 is a diagram of a structural damage detection system 100 according to an embodiment of the present invention.

FIG. 1 shows a structural damage detection system 100 according to an embodiment of the present invention. As shown in FIG. 1, the structure damage detection system 100 comprises a structure damage detection device 110 and a signal processor 120. The structural damage detection device 110 can apply taps on the structure under detection and measure the response signals transmitted from the surface of the structure under detection to structural damage detection device 110. The signal processor 120 can process the response signals measured by the structural damage detection device 110 to determine whether there is damage in the structure under detection and the position of damage.

The structural damage detection device 110 comprises a tapper 112 and a sensor 114 integrated with the tapper 112. The tapper 112 can tap the structure under detection with a tapping force of a predetermined magnitude at a predetermined frequency band while the structural damage detection device 110 is scanning the surface of the structure under detection. The sensor 114 can measure the responses transmitted from the surface of the structure under detection to the tapper. Generally, displacement, velocity and acceleration responses will occur on the surface of the structure under detection due to the impact of the tapping force. Owing to the interaction between the surface of the structure under detection and the tapper, the responses will be transmitted to the tapper, and the magnitude of the instantaneous value can reflect the structural properties of the structure under detection at the tapping position. Therefore, when damage occurs in the structure under detection, the displacement, velocity and acceleration responses at the position of damage transmitted from the surface of the structure under detection to the tapper will differ from those responses at intact positions distinctly, and based on that, the present invention is put forth. The sensor 114 can be any sensor capable of measuring the responses transmitted from the surface of the structure under detection to the tapper. For example, the sensor 114 can be any sensor capable of measuring any one of the displacement, velocity and acceleration responses transmitted from the surface of the structure under detection to the tapper. According to one embodiment of the present invention, the sensor 114 can be an acceleration sensor for measuring the acceleration response transmitted from the surface of the structure under detection to the tapper. The relation between the acceleration a and the structural displacement response b measured by the sensor 114 and the structural local impedance Z and the tapping force F fulfills the following formula:

$$a(x) \approx -\frac{b(x)}{M} Z(x) + \frac{F(x)}{M} - g$$

where x is the tapping position, M is the quality of the tapper, g is the acceleration of gravity.

The signal processor 120 comprises a spectrum acquisition unit 122, a spectrum envelope interception unit 124, a damage indicator calculation unit 126 and a damage position determining unit 128.

The spectrum acquisition unit 122 acquires the sensor signals measured by the sensor 114. According to the requirement of the accuracy of detection, the surface of the structure wider detection can be divided into a plurality of detection portions with a given size, and it takes a certain period of time for the structural damage detection device 110 to scan each portion of the surface, so the signal acquired by the sensor 114 is the sensor signal distribution over this time period. Subsequently, the spectrum acquisition unit 122 can transform the temporal distribution of the sensor signal so as to acquire the representation of the signal in the frequency domain or scale domain. Such transformation can be implemented by any transform process in the prior art, for instance, it can be short time Fourier transformation, wavelet transformation or Hilbert-Huang transformation and so on. Thereby, the spectrum acquisition unit 122 can acquire the frequency spectrum or scale spectrum of signal at each position of the structure surface.

The spectrum envelope interception unit 124 can intercept from the signal spectrum a spectrum envelope corresponding to the frequency band of the tapping force of the tapper. Optionally, only the spectrum corresponding to the tap frequency band of the tapper is intercepted, and then only the signal within the spectrum is analyzed. This can, on one hand, reduce the processing expenses required for processing the entire spectrum of the frequency band, and on the other hand, decrease the influence of the environmental noise on the detection results considerably by setting the tap frequency band with a different frequency band from that of the environmental noise, thereby improving the accuracy of detection.

The damage indicator calculation unit 126 can calculate the damage indicator at each position of the surface of the structure under detection based on the intercepted spectrum envelope. The damage indicator reflects the degree of similarity between the spectrum envelope at one position and the spectrum envelope at other positions. The damage indicated value can be calculated in many ways. In one embodiment, the damage indicated value can be calculated as follows. Firstly, the spectrum envelope is converted into a spectrum vector. This conversion can be done by using the amplitudes at a plurality of frequencies in the acquired spectrum envelope as components of the spectrum vector. The number of the components of the spectrum vector can be determined depending on the accuracy of detection and the processing performance of the system, etc. The frequencies corresponding to the components can be distributed evenly or unevenly within the frequency band of the spectrum envelope. However, for the structure under detection, the way of selecting frequencies at each position should be the same during the process. After the spectrum vector at each position has been generated, the damage indicated value that reflects the degree of similarity between the spectrum vector at current position and the spectrum vector at other positions is calculated. The degree of similarity between two spectrum vectors can be calculated in many ways. In one embodiment, the damage indicated value can be calculated as:

$$\left( \sum_{j=1...n} \frac{Y_i \cdot Y_j}{|Y_i| \times |Y_j|} \right) / n$$

where $Y_i$ and $Y_j$ are the spectrum vectors at the current position and at other positions in the structure respectively, the calculator • is the inner product calculation of the spectrum vector, $|Y_i|$ and $|Y_j|$ are the lengths of the vectors $Y_i$ and $Y_j$, and n is the number of the detection portions divided for the structure under detection. The more similar $Y_i$ and $Y_j$ are, i.e., the more similar shapes envelope i and envelope j have, the closer to 1

$$\frac{Y_i \cdot Y_j}{|Y_i| \times |Y_j|}$$

is. Thus, the damage indicated value for a certain spectrum vector $Y_i$ can be an average of the sum total of the similarity between the spectrum vector $Y_i$ and all the other spectrum vectors $Y_j$.

According to a further embodiment, the MAC coefficient can be used to acquire the damage indicated value. The formula for calculating a MAC coefficient matrix is as follows:

$$MAC(i, j) = \frac{Y_i \cdot Y_j}{|Y_i| \times |Y_j|}$$

where Y.sub.i and Y.sub.j are the spectrum vectors of the ith portion and the jth portion in the structure respectively, the calculator.cndot. is the inner product calculation of the spectrum vector, |Y.sub.i| and |Y.sub.j| are the lengths of the vectors Y.sub.i and Y.sub.j. Each element in the MAC coefficient matrix represents the degree of similarity between two spectrum vectors, wherein the element in the leading diagonal must equal 1. The magnitude of the element in the ith line or the ith column of the MAC coefficient matrix can reflect the damage corresponding to a certain spectrum vector Y.sub.i, so it can be deemed as the damage indicated value of the position corresponding to the spectrum vector Y.sub.i.

The damage position determining unit 128 can determine a position of damage in the structure under detection based on the damage indicator at each position of the surface of the structure under detection. For instance, the damage position determining unit 128 can determine the position where the damage indicated value abruptly drops as a position where damage occurs. This is because if the structure is not damaged, the distribution of the damage indicated value in the space should be very smooth. If the damage indicated value at a certain position changes abruptly, it means that the local impedance at this position differs from the other positions distinctly, so damage may probably occur, and the magnitude of the abrupt change reflects the severity of the damage. For example, a curve can be drawn with the values of the elements in the first line of the MAC coefficient matrix as the elements of a y-axis and the corresponding structure positions as an x-axis. If the structure is not damaged, the curve should be quite smooth; if the curve drops abruptly at a position, it means that damage occurs at this position, and the greater the amplitude of the drop has, the more severe the damage is. In one embodiment, a position where the absolute value of the first derivative of the curve exceeds a predetermined threshold can be determined as a position where damage occurs.

Figure 2:
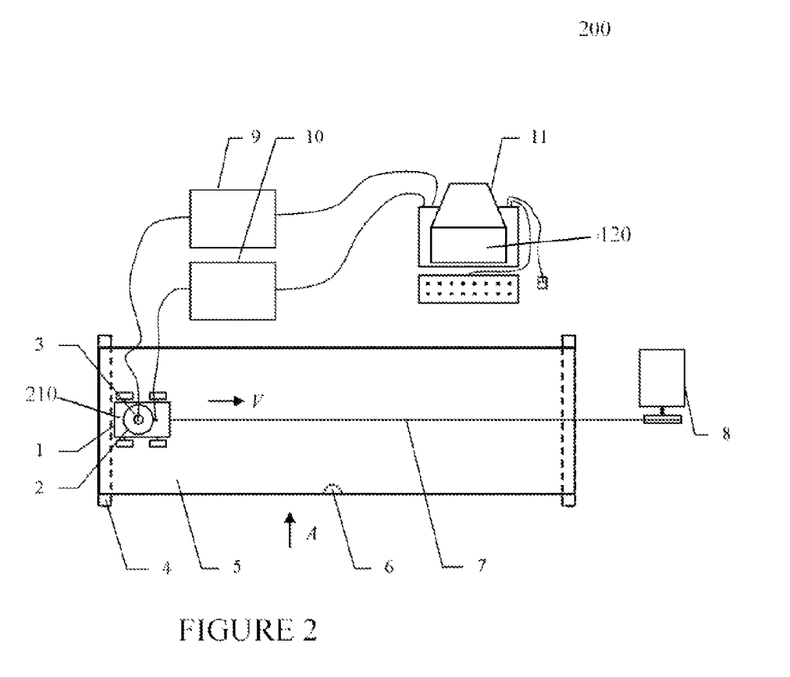
FIG. 2 is a top view of a structural damage detection system 200 according to a further embodiment of the present invention.
Figure 3:
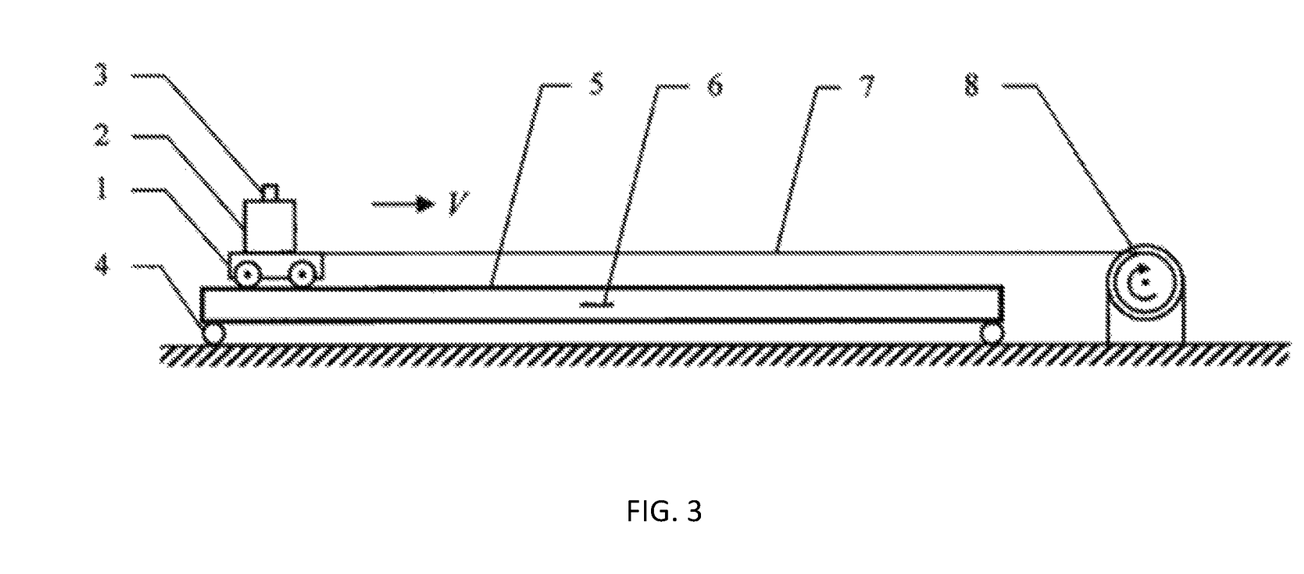
FIG. 3 is a front view of the structural damage detection system 200 along direction A in FIG. 2 according to a further embodiment of the present invention.

FIGS. 2 and 3 show a diagram of a damage detection system 200 according to an embodiment which is applicable for the structural damage detection of bridge like structures. In this embodiment, the structure under detection is a plate structure with an axial length far much larger than the height of section perpendicular to the axis, and the cross-sections of the plate structure along the axial are quite similar to each other. Such a structure is very common in engineering practice, e.g. highway bridges and railway bridges both have such structures. In the engineering practice, such bridges are often required detection to ensure that they are not damaged or that they can be repaired timely when damage occurs so as to avoid accidents due to cracked bridges.

The damage detection system 200 shown in FIGS. 2 and 3 is applicable for the damage detection of the above bridge structures and the like. As shown in FIG. 2, the structure under detection is laminate 5 fixed on two steel sticks 4 on the ground, a certain gap from the ground being provided to make sine that the laminate 5 is not in contact with the ground when the structural damage detection device 210 moves to the central position of the laminate 5, so that the laminate 5 can well simulate a bridge structure in the reality. Besides, in order to detect structure under detection, damage 6 is made in the laminate 5, expressed as a crack. The structural damage detection device 210 can be integrated in a steel car model 1, wherein the tapper 3 can produce a tapping force at a predetermined frequency band under the control of the control signal. In one embodiment, the tapper 3 is a JZK-2 vibration exciter which can produce a tapping force at a predetermined frequency band under the control of the control signal from computer 11. For instance, the DASYLab software in computer 11 can generate control signals synthesized by 16 sine signals with equal amplitude evenly distributed between 90 and 240 Hz, the control signals undergo a digital-to-analogue conversion by the D/A port of an ACL-8112-PG conversion card, and are amplified by YE5871 power amplifier 10 and finally transmitted to the tapper 3 to produce a tapping force at the frequency band of 90-240 Hz.

The sensor 2 in the structural damage detection device 210 is an acceleration sensor which can measure the acceleration signal transmitted from the surface of the structure under detection to the tapper 3 and send it to the signal processor 120 in the computer 11 for further processing. The acceleration sensor 2 can adopt a YD-36 piezoelectric accelerometer, and the signals being collected are input into computer 11 for further processing by the signal processor 120 therein after being amplified by the YE5852T charge amplifier 9 and undergoing the digital-to-analogue conversion by the A/D port of an ACL-8112-PG conversion card. In this case, the acceleration sensor collects signals at a sample rate of 1024 times per second.

The structure of the signal processor 120 is substantially the same as that of the implementation as shown in FIG. 1, so it will not be discussed in detail.

As shown in FIGS. 2 and 3, the car model 1 integrated with the structural damage detection device 210 is placed at the center of the laminate 5 and dragged by a thin steel wire 7 driven by a 41k25RGN-C speed adjustable motor 8 fixed on the ground, and it scans along the length direction (i.e. axially) of the laminate 5 at a speed of V=1.3 cm/s. During the scanning, it taps with a tapping force at a frequency band of 90-240 Hz generated by the tapper 3, and meanwhile, the acceleration sensor 2 collects the acceleration signals to send them to the signal processor 120 for further processing.

In the embodiment, the laminate 5 is divided along the length direction, with 1.3 cm as a unit. As the car model moves at a speed of 1.3 cm/s and the acceleration sensor collects signals at a sample rate of 1024 times per second, the spectrum acquisition unit 122 acquires the measured signals with 1024 acceleration signals and obtains the frequency spectrum by means of the short time Fourier transformation. The spectrum envelope interception units 124 intercepts the spectrum envelope corresponding to the frequency band of the tapping force, i.e. the frequency band of 90-124 Hz. The damage indicated value calculation unit 126 selects frequencies of 90 Hz, 100 Hz, 110 Hz . . . , 240 Hz as the frequencies corresponding to the components in the spectrum vector, i.e., the damage indicated value calculation unit 126 vectorizes the spectrum envelope as vectors with a length of 16. Then, the damage indicated value calculation means 126 calculates the MAC coefficient matrix:

$$MAC(i, j) = \frac{Y_i \cdot Y_j}{|Y_i| \times |Y_j|}$$

Subsequently, the damage position determining unit 128 can determine the position of damage based on the value of the MAC coefficient matrix.

Figure 4:
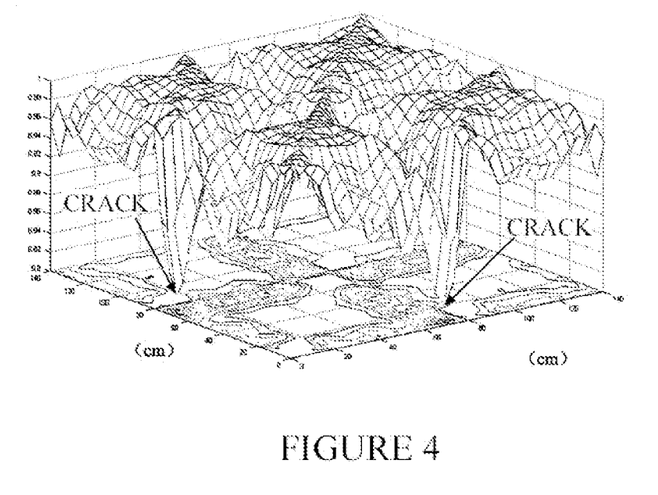
FIG. 4 is an illustration of the distribution map of the MAC matrix elements.

FIG. 4 shows the distribution map of the MAC matrix elements, which is the result acquired by the detection of a laminate having a size of 140×15×3 cm with an artificially made crack 6 which is 2 cm long. It can be seen obviously from FIG. 4 that the MAC coefficient at the crack is distinctly lower than the MAC coefficient at the other positions, which proves that the method according to the present invention can detect damage of the structure effectively.

Figure 5:
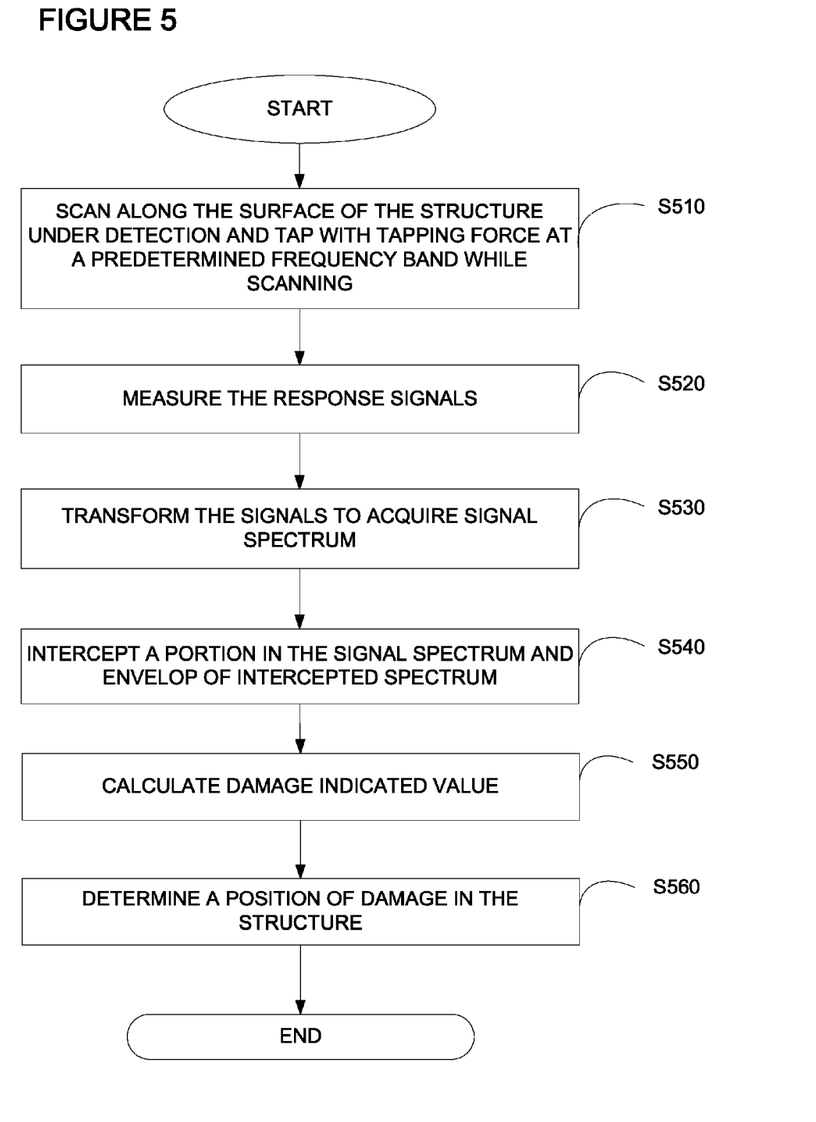
FIG. 5 shows a flow chart of a structural damage detection method according to an embodiment of the present invention.

FIG. 5 shows a flow chart of a structural damage detection method according to an embodiment of the present invention. As shown in FIG. 5, the method begins with step S510 where the tapper in the structural damage detection device scans along the surface of the structure under detection, wherein the tapper taps with the tapping force at a predetermined frequency band while scanning. Subsequently, in step S520, the sensor in the structural damage detection device measures the response signals of the tapper. As mentioned in the structural damage detection device, the measured signals can be any response signals transmitted from the surface of the structure under detection to the tapper at the tapping position. For instance, the signal measured by the sensor can be displacement, velocity or acceleration. In particular, when the signal measured by the sensor is an acceleration signal, it is easier to be applicable in practice. In Step S530, the signals measured by the sensor are transformed so as to acquire the signal spectrum at each position of the surface of the structure under detection. The surface of the structure under detection is divided into many portions upon the requirement of the accuracy of detection. The signal measured in each portion is a distribution of the signals over a time period which is taken by the structural damage detection device to scan the portion, so the distribution of the signal in the time domain can be transformed to acquire the representation of the signal in the frequency domain or scale domain. Such transformation can be implemented by any transformation in the prior art, for instance, it can be short time Fourier transformation, wavelet transformation or Hilbert-Huang transformation and so on.

After that, in step S540, a portion in the signal spectrum that corresponds to the predetermined frequency band of the tapping force of the tapper is intercepted and the envelope of the intercepted spectrum is acquired. As mentioned before, the structural damage detection method only intercepts the spectrum corresponding to the tap frequency band of the tapper, and then only analyzes the signal within the spectrum of the frequency band.

In step S550, the damage indicated value at each portion of the surface of the structure under detection is calculated based on the intercepted spectrum envelope, the damage indicator reflecting the degree of similarity between the spectrum envelope at a position and the spectrum envelope at other positions. The damage indicated value can be calculated in many ways.

In one embodiment, the damage indicated value can be calculated as follows:

1. The spectrum envelope is converted into a spectrum vector, and the conversion can be implemented by acquiring the amplitude at different frequencies in the spectrum envelope as the components of the spectrum vector. The number of the components of the spectrum vector can be determined depending on the accuracy of the detection and the processing performance of the system, etc. The frequencies corresponding to the components can be distributed evenly or unevenly within the frequency band of the spectrum envelope. However, for the structure under detection, the way of selecting frequencies at each position should be the same throughout this method;

2. After the spectrum vector at each position has been generated, a damage indicated value reflecting the degree of similarity between the spectrum envelope at the current position and the spectrum envelope at other positions is calculated. The degree of similarity between two spectrum vectors can be calculated in many ways. In one embodiment, the damage indicated value can be calculated as:

$$\left(\sum_{j=1\ldots n} \frac{Y_i \cdot Y_j}{|Y_i| \times |Y_j|}\right)/n$$

where $Y_i$ and $Y_j$ are the spectrum vectors at the current position i and at other position j in the structure respectively, the calculator • is the inner product calculation of the spectrum vector, $|Y_i|$ and $|Y_j|$ are the lengths of the vectors $Y_i$ and $Y_j$, and n is the number of the detection portions divided for the structure under detection. The more similar $Y_i$ and $Y_j$ are, i.e., the more similar shapes envelope i and envelope j have, the closer to 1

$$\frac{Y_i \cdot Y_j}{|Y_i| \times |Y_j|}$$

is. Thus, the damage indicated value for a certain spectrum vector $Y_i$ can be an average of the sum total of the similarity between the spectrum vector $Y_i$ and all the other spectrum vectors $Y_j$.

According to a further embodiment, the MAC coefficient can be used to acquire the damage indicated value. The formula for calculating a MAC coefficient matrix is as follows:

$$MAC(i, j) = \frac{Y_i \cdot Y_j}{|Y_i| \times |Y_j|}$$

where $Y_i$ and $Y_j$ are the spectrum vectors of the ith portion and the jth portion in the structure respectively, the calculator • is the inner product calculation of the spectrum vector, $|Y_i|$ and $|Y_j|$ are the lengths of the vectors $Y_i$ and $Y_j$. Each element in the MAC coefficient matrix represents the degree of similarity between two spectrum vectors, wherein the element in the leading diagonal of the matrix must equal 1. The magnitude of the element in the ith line or the ith column of the MAC coefficient matrix can reflect the damage corresponding to a certain spectrum vector $Y_i$, so it can be determined as the damage indicated value of the position corresponding to the spectrum vector $Y_i$.

After the damage indicated value has been calculated at each position of the surface of the structure under detection, in step S560, a position of damage in the structure under detection is determined based on the damage indicator at each position of the surface of the structure under detection. For instance, the position where the damage indicated value abruptly drops can be determined as a position where damage occurs. For example, a curve is drawn with the values of the elements in the first line of the MAC coefficient matrix as the elements of a y-axis and the corresponding structure positions as an x-axis. If the structure is not damaged, the curve should be quite smooth; if the curve drops abruptly at a position, it means that damage occurs at this position, and the greater the amplitude of the drop has, the more severe the damage is. In one embodiment, a position where the absolute value of the first derivative of the curve exceeds a predetermined threshold can be determined as a position where damage occurs.

It should be noted that in the signal processor of the structural damage detection device according to the present invention, components therein are logically divided in light of the functions to be achieved. However, the present invention is not limited by this and the components of the signal processor can be redivided or recombined upon requirement, for instance, some components can be combined as an individual component or some components can be further divided into more sub-components.

The embodiment of the signal processor according to the present invention can be carried out by hardware or by software modules run on one or more processors, or by the combination of the two. One skilled in the art should understand that microprocessors or digital signal processors (DSP) can be used in practice to carry out some or all of the functions of some or all of the components of the signal processor. The present invention can further be implemented as device or programs (for example, computer programs and computer program products) for executing part or all of the method described herein. Such programs carrying out the present invention can be stored in a computer-readable medium.

It should be noted that the above embodiments illustrate rather than limit the invention, and that those skilled in the art will be able to design alternatives without departing from the scope of the appended claims. In the claims, any reference signs placed between parentheses shall not be construed as limiting the claim. The word "comprise" does not exclude the existence of elements or steps other than those listed in a claim. The word "a" or "an" preceding an element does not exclude the existence of a plurality of such elements. The present invention can be achieved by means of hardware comprising several different elements and by means of an appropriately programmed computer. In unit claims listing several means, several of these means can be embodied by one and the same item of hardware. The use of ordinal words such as first, second and third does not represent any order, but instead, they can be understood as titles.

The invention claimed is:

1. A structural damage detection method for detecting damage of a structure, comprising:
   scanning along a structure surface with a tapper, wherein the tapper taps with a tapping force at a predetermined frequency band while scanning;
   measuring tapping response signals transmitted from the structure surface to the tapper at positions of the structure surface by a sensor, wherein the tapping response signals measured by the sensor comprises at least one of displacement, velocity, and acceleration;
   transforming the tapping response signals measured by the sensor to acquire a signal spectrum at each of the positions of the structure surface;
   intercepting from the signal spectrum a spectrum envelope corresponding to the predetermined frequency band of the tapping force;
   calculating a damage indicated value at the position of the structure surface, said calculated damage indicated value reflecting a degree of similarity between the spectrum envelope at each of the positions and the spectrum envelope at other positions; and
   determining a position where the damage indicated value changes abruptly as a position of structural damage;
   wherein calculating the damage indicated value at each of the positions of the structure surface comprises: generating a spectrum vector corresponding to the spectrum envelope at each of the positions, wherein each component of the spectrum vector comprises the spectrum value corresponding to a certain frequency in the spectrum envelope;
   calculating a damage indicated value to reflect the degree of similarity between the spectrum vector at one position, represented by i, and the spectrum vector at other positions, represented by j, comprises: calculating the damage indicated value as:

$$\left( \sum_{j=1...n} \frac{Y_i \cdot Y_j}{|Y_i| \times |Y_j|} \right) / n$$

where $Y_i$ and $Y_j$ are the spectrum vectors at said one position and at other positions in the structure respectively, a calculator • is an inner product calculation of the spectrum vector, $|Y_i|$ and $|Y_j|$ are lengths of the vectors $Y_i$ and $Y_j$, and n is the number of the measured positions in the structure.

2. The method according to claim 1, further comprises: determining a severity of the damage based on a degree of an abrupt change of the damage indicated value.

3. The structural damage detection method according to claim 1, wherein the sensor and the tapper are integrated together.

4. The structural damage detection method according to claim 1, wherein the calculation of the damage indicated value which reflects the degree of similarity between the spectrum vector at one position and the spectrum vector at other positions comprises: calculating a MAC coefficient matrix as:

$$MAC(i, j) = \frac{Y_i \cdot Y_j}{|Y_i| \times |Y_j|}$$

where $Y_i$ and $Y_j$ are the spectrum vectors of the ith portion and the jth portion in the structure respectively, a calculator • is an inner product calculation of the spectrum vector, $|Y_i|$ and $|Y_j|$ are lengths of the vectors $Y_i$ and $Y_j$; and determining the damage indicated value at the position based on the relative magnitude of the element in a line or a column of the MAC coefficient matrix corresponding to the position.

5. The structural damage detection method according to claim 1, wherein the structure has an elongated shape, wherein each section is similar along the axial of the structure, wherein the tapper scans along the surface of the structural axially, and wherein the sensor measures the response signals at each position of the structure axially.

6. The structural damage detection method according to claim 1, wherein the sensor is a sensor for measuring the acceleration response transmitted from the structure surface to the tapper.

7. A structural damage detection device, comprising:
   a tapper being configured to tapping on a surface of the structure under detection with, a tapping force at a predetermined frequency band;
   a sensor being configured to measure tapping response signals transmitted from the surface of the structure under detection to the tapper, wherein the tapping response signals measured by the sensor comprises at least one of displacement, velocity and acceleration;
   wherein the tapper and the sensor are integrated together, so that the sensor measures the tapping response signals transmitted from the surface of the structure under detection to the tapper while the tapper is tapping on the surface of the structure under detection;
   a signal processor being configured, to process the signals measured by the sensor in the structural damage detection device so as to determine a position of damage in the structure under detection, the signal processor being configured to execute programs comprising instructions to perform the following:
   transform the signals measured by the sensor so as to acquire the signal spectrum at positions of the structure surface;
   intercept from the signal spectrum a spectrum envelope corresponding to the predetermined frequency band of the tapping force;
   calculate a damage indicated value at each of the positions of the surface of the structure, the damage indicated value reflecting a degree of similarity between the spectrum envelope at one position and the spectrum envelope at other positions; and determine a position of damage in the structure based on the damage indicator at each of the positions of the surface of the structure;

wherein the signal processor generates a spectrum vector corresponding to the spectrum envelope at a corresponding position, wherein each component of the spectrum vector comprises the spectrum value corresponding to a certain frequency in the spectrum envelope;

wherein the signal processor calculates the damage indicated value to reflect the degree of similarity between the spectrum vector at the current position and the spectrum vector at other positions; and wherein the signal processor calculates the damage indicated value as:

$$\left( \sum_{j=1...n} \frac{Y_i \cdot Y_j}{|Y_i| \times |Y_j|} \right) / n$$

where $Y_i$ and $Y_j$ are the spectrum vectors at one position, represented by i, and at other positions, represented by j, in the structure respectively, a calculator • is an inner product calculation of the spectrum vector, $|Y_i|$ and $|Y_j|$ are lengths of the vectors $Y_i$ and $Y_j$, and n is the number of the measured positions in the structure.

8. The structural damage detection device according to claim 7, wherein the sensor can be an acceleration sensor.

9. The structural damage detection system according to claim 7, wherein the damage indicated value calculator is configured to: calculate a MAC coefficient matrix, the MAC coefficient matrix being calculated as:

$$MAC(i, j) = \frac{Y_i \cdot Y_j}{|Y_i| \times |Y_j|}$$

where $Y_i$ and $Y_j$ are the spectrum vectors of the ith portion and the jth portion in the structure respectively, a calculator • is an inner product calculation of the spectrum vector, and $|Y_i|$ and $|Y_j|$ are lengths of the vectors $Y_i$ and $Y_j$; and determine the damage indicated value at the position based on the relative magnitude of the element in a line or a column of the MAC coefficient matrix corresponding to the position.

10. The structural damage detection system according to claim 7 wherein the structure under detection has an elongated shape, wherein each section is similar along the structure under detection axially, wherein the tapper scans along the surface of the structural under detection axially, and wherein the sensor measures the response signals transmitted from the surface of the structured under detection to the tapper at each position of the structure under detection axially.

11. A structural damage detection method for detecting damage of a structure, comprising:
    scanning along a structure surface with a tapper, wherein the tapper taps with a tapping force at a predetermined frequency band while scanning;
    measuring tapping response signals transmitted from the structure surface to the tapper at positions of the structure surface by a sensor, wherein the tapping response signals measured by the sensor comprises at least one of displacement, velocity, and acceleration;
    transforming the tapping response signals measured by the sensor to acquire a signal spectrum at the position of the structure surface;
    intercepting from the signal spectrum a spectrum envelope corresponding to the predetermined frequency band of the tapping force;
    calculating a damage indicated value at each of the positions of the structure surface which reflecting a degree of similarity between the spectrum envelope at each of the positions and the spectrum envelope at other positions; and
    determining a position where the damage indicated value changes abruptly as a position of structural damage;
    wherein calculating the damage indicated value at each of the positions of the structure surface comprises: generating a spectrum vector corresponding to the spectrum envelope at each of the positions, wherein each component of the spectrum vector is the spectrum value corresponding to a certain frequency in the spectrum envelope;
    calculating the damage indicated value to reflect the degree of similarity between the spectrum vector at one position and the spectrum vector at other positions by calculating a MAC coefficient matrix as:

$$MAC(i, j) = \frac{Y_i \cdot Y_j}{|Y_i| \times |Y_j|}$$

where $Y_i$ and $Y_j$ are the spectrum vectors of the ith position and the jth position in the structure respectively, a calculator • is an inner product calculation of the spectrum vector, $|Y_i|$ and $|Y_j|$ are lengths of the vectors $Y_i$ and $Y_j$; and determining the damage indicated value at the ith or jth position based on the relative magnitude of the element in a line or a column of the MAC coefficient matrix corresponding to the ith or ith position.

* * * * *